United States Patent
Pan et al.

(10) Patent No.: US 12,161,765 B2
(45) Date of Patent: Dec. 10, 2024

(54) COMPOSITIONS AND METHODS FOR REMOVING BIO-SYNTHETIC NANO-PARTICLES FROM BODILY FLUIDS

(71) Applicants: KaloCyte, Inc., Baltimore, MD (US); University of Maryland, Baltimore, Baltimore, MD (US); University of Maryland, Baltimore County, Baltimore, MD (US)

(72) Inventors: Dipanjan Pan, Ellicot City, MD (US); Allan Doctor, Towson, MD (US); Nivesh Mittal, Baltimore, MD (US)

(73) Assignees: KaloCyte, Inc., Baltimore, MD (US); University of Maryland, Baltimore, Baltimore, MD (US); University of Maryland, Baltimore County, Baltimore, MD (US)

( * ) Notice: Subject to any disclaimer, the term of this patent is extended or adjusted under 35 U.S.C. 154(b) by 0 days.

(21) Appl. No.: 17/692,289

(22) Filed: Mar. 11, 2022

(65) Prior Publication Data

US 2022/0287984 A1    Sep. 15, 2022

Related U.S. Application Data

(60) Provisional application No. 63/159,547, filed on Mar. 11, 2021.

(51) Int. Cl.
| | |
|---|---|
| *A61K 9/51* | (2006.01) |
| *A61F 2/06* | (2013.01) |
| *A61K 9/19* | (2006.01) |
| *B82Y 5/00* | (2011.01) |

(52) U.S. Cl.
CPC ............ *A61K 9/5161* (2013.01); *A61F 2/064* (2013.01); *A61K 9/19* (2013.01); *B82Y 5/00* (2013.01)

(58) Field of Classification Search
CPC .............. A61K 9/51; A61K 9/19; B82Y 5/00
See application file for complete search history.

(56) References Cited

U.S. PATENT DOCUMENTS

| | | | | |
|---|---|---|---|---|
| 4,169,079 A | * | 9/1979 | Tabushi | C08F 8/30 502/402 |
| 2004/0147033 A1 | | 7/2004 | Shriver et al. | |
| 2013/0109934 A1 | * | 5/2013 | Hyde | A61P 35/04 600/314 |
| 2014/0065205 A1 | | 3/2014 | Anthony et al. | |
| 2017/0181424 A1 | * | 6/2017 | Lanza | A61P 7/08 |
| 2017/0312363 A1 | | 11/2017 | Weng et al. | |
| 2018/0214561 A1 | | 8/2018 | Weng et al. | |

FOREIGN PATENT DOCUMENTS

CN           111134116           5/2020

OTHER PUBLICATIONS

Gan, Z., et al., "Nanoparticles containing constrained phospholipids deliver mRNA to liver immune cells in vivo without targeting ligands", Bioengineering and Translational Medicine, pp. 1-11 (Year: 2020).*
Cosco, D., et al., "Polysaccharide-coated liposomes by post-insertion of a hyaluronan-lipid conjugate", Colloids and Surfaces B. Biointerfaces, pp. 119-126 (Year: 2017).*
Laverman,P. etal., "Improved imaging of Infections by Avidin-Induced Clearance of 99mTc@Biotin@PEGLiposomes", J. Nuclear. Medicine.,pp. 912-918. (Year: 2000).*
International Search Report issued in copending International Patent Application No. PCT/US22/19872 on Jun. 9, 2022.

* cited by examiner

*Primary Examiner* — Michael G. Hartley
*Assistant Examiner* — Jagadishwar R Samala
(74) *Attorney, Agent, or Firm* — Whiteford, Taylor & Preston, LLP; Peter J. Davis

(57) ABSTRACT

Bait and capture methods and compositions for removing bio-synthetic nano-particles from body fluids. Bio-synthetic nano-particles are baited with one-half of a bait and capture complex and lyophilized. The baited bio-synthetic nano-particle is reconstituted and administered to a subject for diagnostic or therapeutic purposes. To remove the bio-synthetic nano-particle from the body, the body fluid containing the baited bio-synthetic nano-article is contacted with the capture portion of the bait and capture complex. The body fluid from which the bio-synthetic nano-particles have been removed may be returned to the subject.

6 Claims, 12 Drawing Sheets

(A) Metabolic Panel

| Parameter | Blank (1:3 PBS: Plasma) | ErythroMer Conc. in Plasma 1 x 10^6 particles/mL | ErythroMer Conc. in Plasma 1.3 x 10^11 particles/mL |
|---|---|---|---|
| Calcium (mg/dL): | 1 (5.5) | 0.81 ± 0.8 (4.5) | 1.01 ± 1.0 (5.6) |
| Anion Gap (mmol/L): | 1 (11.6) | 1.61 ± 19.4 (18.7) | 1.29 ± 11.0 (15.0) |
| Hemolysis Index: | 1 (15.0) | 1.0 ± 0.0 (15.0) | 66.67 ± 0.0 (1000.0) |

(B) CBC Panel

| Parameter | Blank (1:3 PBS: Blood) | ErythroMer 1 x 10^6 particles/mL | ErythroMer Conc. 1.3 x 10^11 particles/mL |
|---|---|---|---|
| WBC (x10^3/uL) | 1 (3.32) | 0.97±0.03 (3.2) | 0.98±0.07 (3.2) |
| RBC (x10^6/uL) | 1 (3.9) | 0.98±0.02 (3.9) | 0.99±0.007 (3.9) |
| Hgb (g/dL) | 1 (8.18) | 0.97±0.01 (8.0) | 1.24±0.018 (10.2) |
| Hct (%) | 1 (24.75) | 0.99±0.02 (24.4) | 0.96±0.005 (24.0) |
| Plt (x10^6/uL) | 1 (47.8) | 0.64±29 (28.4) | 0.965±0.27 (43.0) |

FIG. 2 CONTINUED

|  | Before lyophilization | Reconstitution (4 d) | Reconstitution (14 d) |
|---|---|---|---|
| Size | 131.1±69.8nm | 142.5±84.5nm | 161.8±94.6nm |
| Particle conc | 7.9E+11/mL | 5.6E+11/mL | 5.7E+11/mL |
| Zeta potential | -24.03±0.28mV | -24.32±0.42mV | -18.09±0.22mV |
| Free Hb | 7.76% | 10.10% | 10.83% (1), 7.89% (2) |

FIG. 8

COMPOSITIONS AND METHODS FOR REMOVING BIO-SYNTHETIC NANO-PARTICLES FROM BODILY FLUIDS

FIELD OF THE INVENTION

The present invention relates to methods and compositions for removing and/or separating out bio-synthetic nanoparticless from body fluids and other solutions.

DESCRIPTION OF THE BACKGROUND

There is need for an artificial oxygen ($O_2$) carrier for use when banked blood is unavailable or undesirable. To address this need, the inventors developed ErythroMer (EM), a first-in-class, bio-synthetic, nano-cyte blood substitute. EM is a self-assembled, deformable, hybrid lipid-oligomer based nanoparticle that incorporates high per particle payloads of hemoglobin (Hb) (FIG. 1). The 'artificial cell' design has yielded a prototype that emulates key elements of red blood cell (RBC) physiology and represents an innovative addition to transfusion medicine. To date, efforts to develop Hb-based oxygen carriers (HBOCs) have failed, because of design flaws which do not preserve physiologic interactions of RBCs, in particular: HBOCs capture $O_2$ in lungs, but do not release $O_2$ effectively to tissue, and HBOCs trap endothelial nitric oxide (NO), causing vasoconstriction. The EM design (FIG. 1) surmounts these weaknesses by: 1) encapsulating Hb in a nanoparticle with novel geometry, with an optimized surface area to volume ratio, 2) controlling $O_2$ capture/release with a novel shuttle for a small-molecule designed to lower Hb $O_2$ affinity (RSR13, efaproxiral), 3) attenuating NO uptake through shell properties, and 4) retarding methemoglobin (metHb) formation by co-packaging a reduction system. Moreover, 5) EM is designed for sterile lyophilization and is amenable to facile reconstitution after extended, ambient dry storage. EM offers a pragmatic approach to a complex need and is designed for cost-effective production at scale.

The EM prototype has passed rigorous initial ex vivo and in vivo "proof of concept" testing. $O_2$ delivery has been demonstrated in a novel murine model that reports post-transfusion cellular $O_2$ delivery using a transgenic hypoxia inducible factor (HIF-1α) bioluminescent construct. EM is also being validated in rabbit models of hemorrhagic shock and polytrauma.

SUMMARY OF THE INVENTION

Because EM introduces an acellular form of hemoglobin into the plasma portion of the circulation, it introduces unique challenges to the clinical laboratory because of serum and plasma color interference or because of the nanoparticle shell itself. Blood specimens obtained during the period that ErythroMer is present in vivo appear hemolyzed. Although, hemolysis is a well-understood problem in the clinical laboratory, patients receiving ErythroMer may achieve free hemoglobin concentrations that exceed those seen with typical hemolysis. In addition, ErythroMer is a nanoparticle that may impact light-scattering analysis methods which cannot be practically avoided during analysis, save for developing a blank prior to analysis or by removing the particle entirely.

EM is designed to be used in chiefly at the point of injury to bridge to a clinical setting where further lifesaving care is performed. To manage trauma in clinical settings, complete blood count (CBC) and comprehensive metabolic panels (CMP) are performed to assess the amounts and concentrations of various cells, proteins, and substances in blood which impact the blood's ability to acutely sustain life by delivering oxygen and energy to the rest of the body. Assessments of hemoglobin abundance (oxygen carrying capacity), platelet abundance (clotting ability), and hematocrit (hemoglobin as a percent of whole blood) are impacted by EM. These assessments are taken every 15 to 30 minutes in patients experiencing blood loss and considered alongside changes in blood pressure to determine need for further transfusion in the clinical setting. Preliminary data shows that EM strongly interferes with the optical methods used to determine CBC (FIG. 2B) and CMP (FIG. 2A, C). Therefore, there is an urgent need for a strategy for selective removal of EM from blood specimens.

The present invention is directed toward a robust 'bait and capture' strategy to efficiently remove EM from whole blood specimens based on supramolecular assembly based on host-guest interaction of adamantane ("ADM") and β-CD. This targeted capture strategy comprises adamantane tagged EM as the 'bait' and β-CD functionalized PS beads as the capture model. (FIG. 4) According to the invention, EM presenting with ADM functionalities forms a strong inclusion complex with surface abundant β-CD functionalities on a resin and enables selective removal of the EM from the blood. The choice of ADM and β-CD as 'bait and capture' pair is deliberate because of their strong binding affinity (K=$5.2 \times 10^4$ M−1) and excellent biological compatibility. The carbonaceous ADM is known to induce minimal biological response, whereas β-CD forms stronger inclusion complex with the molecule in comparison to other ubiquitous biological substances, e.g. human serum albumin, globulin etc.

According to further embodiments of the invention, the adamantane-tagged EM is lyophilized for packaging, transport and/or storage. The lyophilized adamantane-baited EM is a powder comprising EM amphiphilic precursor, cholesterol and PEG-PE hemoglobin and allosteric effector, the adamantane tag, and optionally also including cryoprotectants. Reconstitution at the original EM production concentration (or concentrated) is achieved with PBS/water by simple mixing.

Thus, the invention presents a uniquely designed targeted capture strategy to address the unmet need of removing EM from whole blood specimens for the clinical monitoring of blood samples. Notwithstanding the foregoing, and the examples provided herein, it is understood that the targeted capture strategy and compositions described herein may be used to remove any type of bio-synthetic nanoparticles from whole blood, other body fluids, and any other solution. The lyophilized bait tagged EM composition of the present invention may be packaged, stored, transported, for example, in the form of pre-filled tubes or other containers for reconstitution at the site of use. Similarly, the capture composition may be packaged in the form of hemoperfusion cartridges for removing tagged EM from the bloodstream in living patients via extracorporeal circuits, e.g., dialysis systems, CPB systems, and the like. Additionally, the capture composition may be used to remove tagged EM from perfusate in ex vivo organ/organoid preparations.

BRIEF DESCRIPTION OF THE DRAWINGS

FIG. 8 shows various properties of an AM-tagged EM particle according to an embodiment of the invention before lyophilization, four days after reconstitution, and 14 days after reconstitution.

DETAILED DESCRIPTION

Figure 1A:
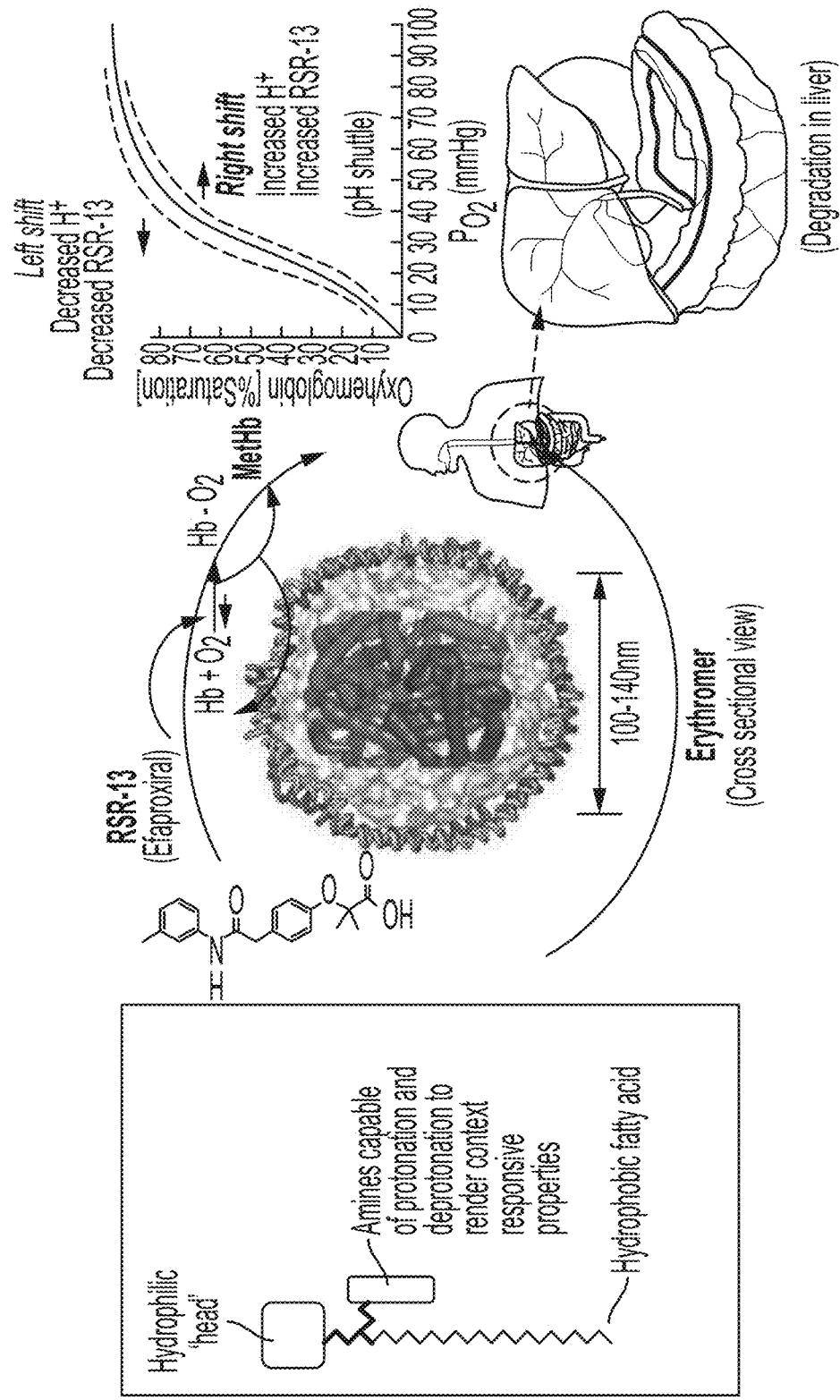
FIGS. 1A and 1B are representations of the ErythroMer (EM) V2 design, features and benefits relative to HBOCs, in which the amphiphilic precursor comprises (a) pH responsive groups that control availability of the allosteric effector (RSR13), enabling context-responsive control of $O_2$ binding and (b) a negatively charged 'head' facilitating biocompatibility of the exofascial surface. The construct mimics endogenous biomolecules and is subject to enzymatic digestion and complete degradation in vivo to end-products identical to that of 'natural' peptides and lipids.
Figure 1B:
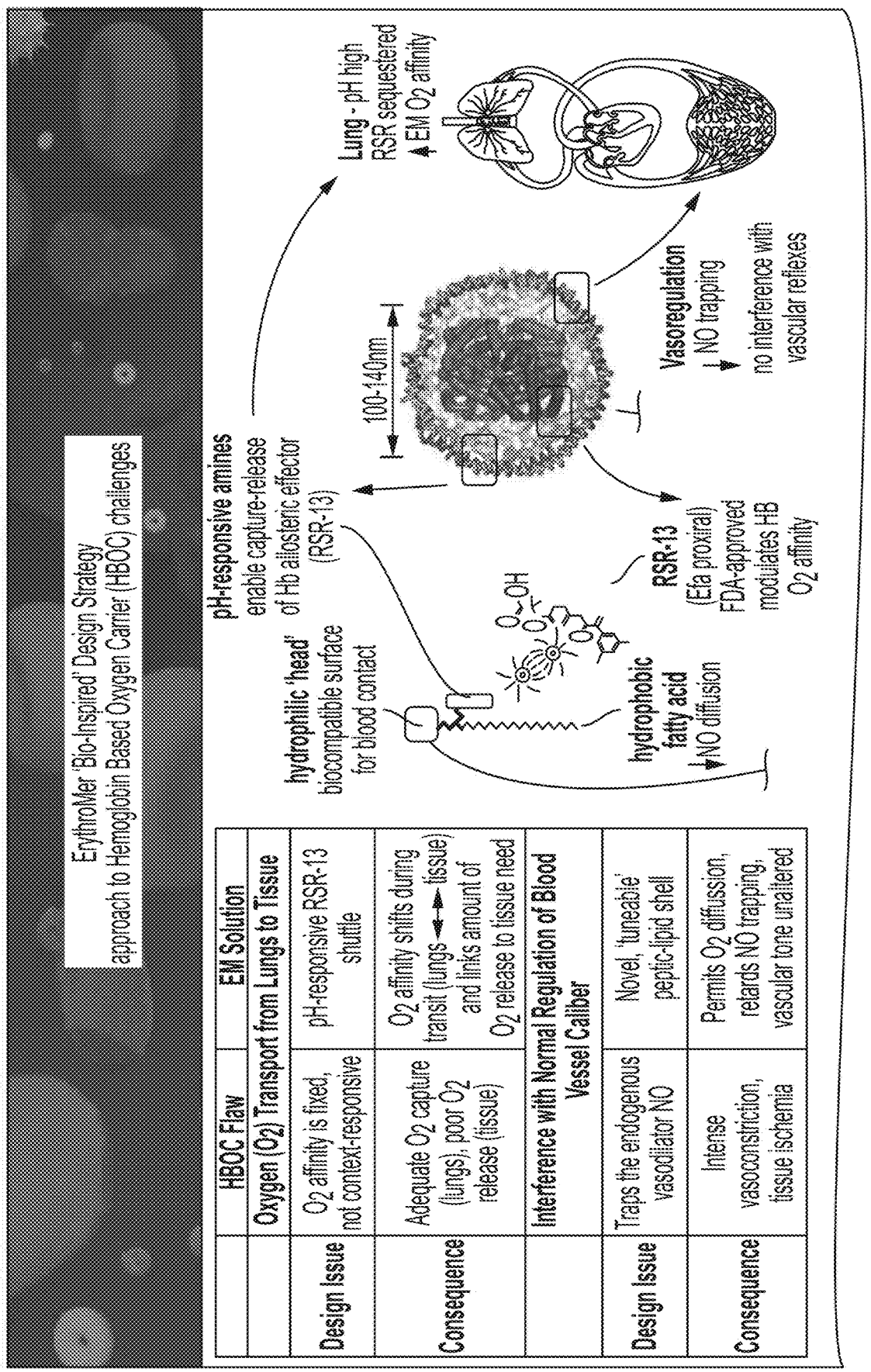
Figure 1B:
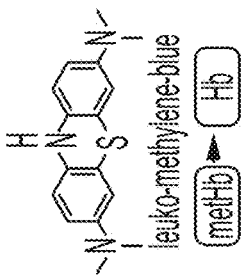
Figure 2:
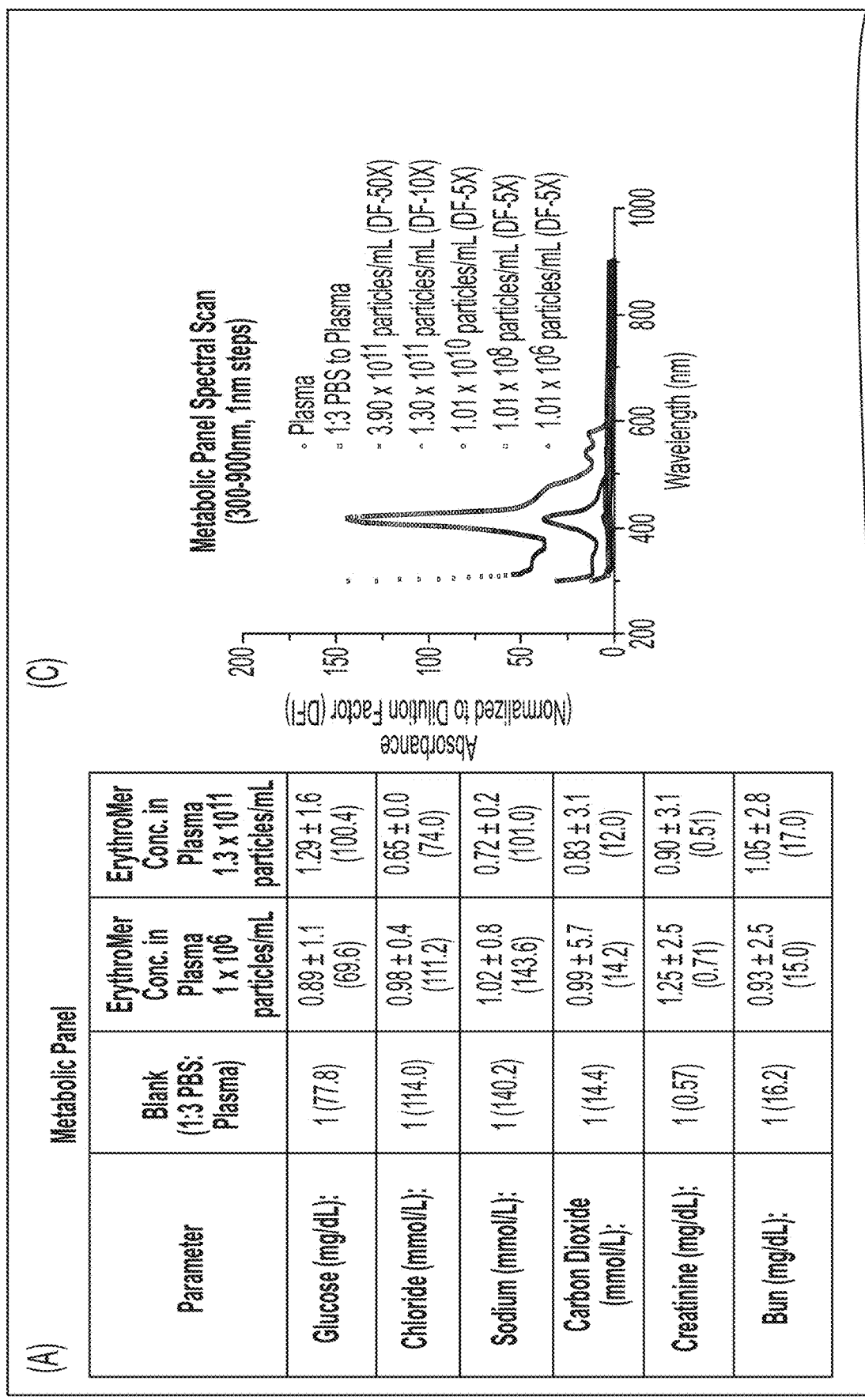
FIG. 2 shows EM interference results: (A) metabolic panel and (B) CBC panel of human plasma with and without EM; (C) overlaid metabolic panel spectral scan (300-900 nm).
Figure 3:
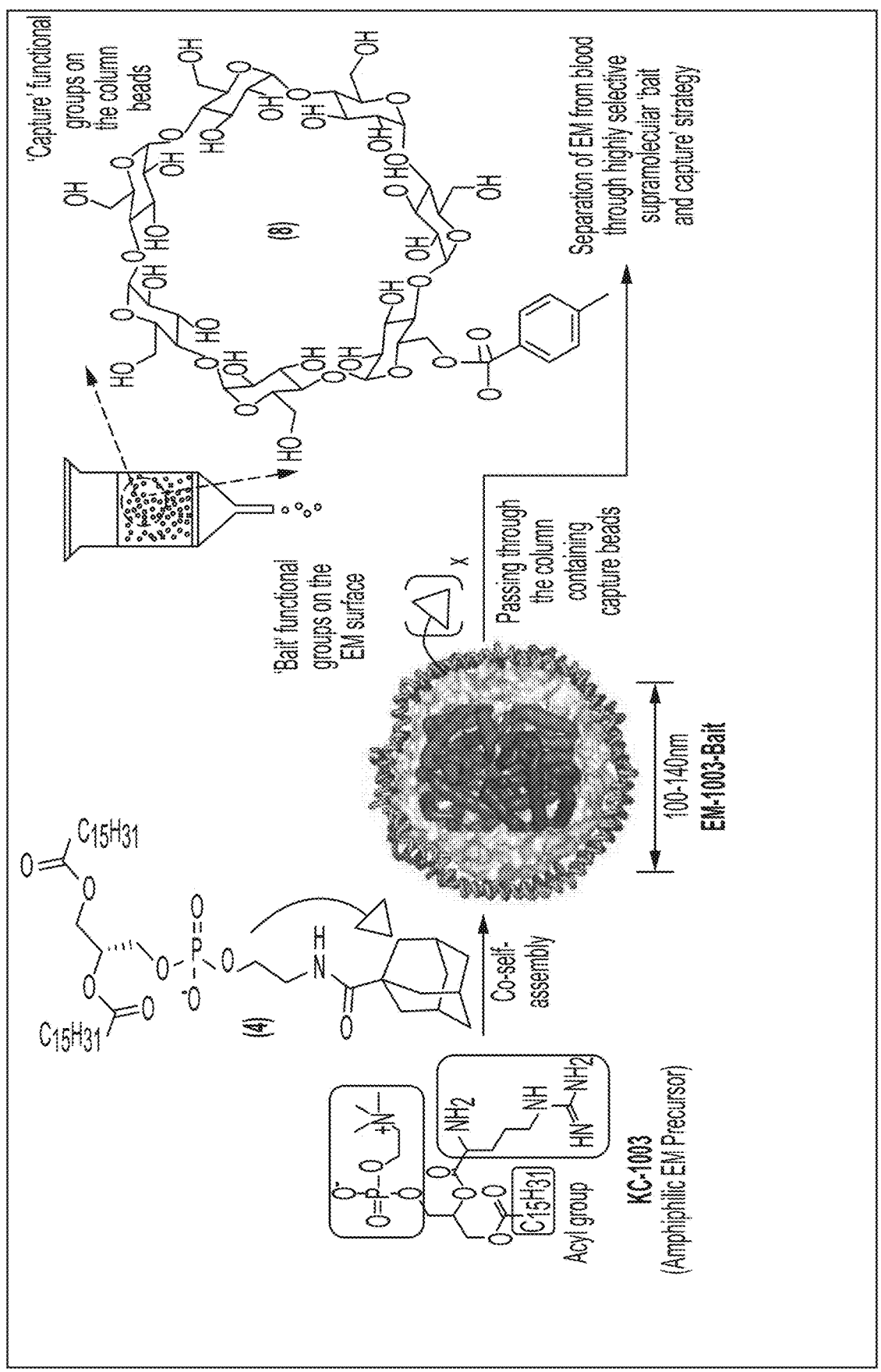
FIG. 3 is a representation of the Bait and Capture design strategy according to an embodiment of the invention. The amphiphilic precursor KC01003 will be co-self-assembled with adamantane-PE (4) to prepare EM-1003 presented with 'bait' functionalities on the surface. The surface coverage is optimized to have minimum numbers of 'bait' molecules to avoid detrimental biological effects. The column is packed with polystyrene (PS) beads conjugated with β-cyclodextrin functionalities. Highly selective interaction between adamantane and β-cyclodextrin through host-guest chemistry enables efficient separation of EM from blood.

According to embodiments of the invention, there is presented a bio-engineered and scalable approach to remove EM from whole blood specimens. (FIG. 3) The proposed supramolecular approach offers several advantages, e.g. (i) facile formation of the inclusion complex under ambient condition makes the pilot-scale study feasible without introducing any special genetic or biochemical techniques; (ii) the relatively small molecular adamantane ("ADM") tag is expected to have little to none effect on the EM structures and functions and (iii) the optimal ratio of β-cyclodextrin (β-CD) functionalization on polystyrene (PS) beads introduces insignificant changes to the pore size of the column beads and hence safely clear the blood stream. The present invention will pave the pathway for the translation of artificial RBCs. According to further embodiments of the invention, the bait and capture design is optimized for usability at point of care settings. This involves mechanisms to effectively remove ErythroMer from the patient blood samples, with minimal disruption to already existing blood collection and sample processing techniques, including. customizing already existing blood collection tubes to be able to capture and retain ErythroMer in the tube itself, leaving whole blood components free for further analysis. This entails a comprehensive development of immobilizing the capture system in the blood collection tube, titrated to a concentration to effectively remove EM specifically and fully from the blood, keeping in mind the goal that the blood collection tubes with the special capture functionality are scalable and can be manufactured commercially with minimal changes to their existing method of manufacturing. Concurrently, the bait is compatible with the lyophilization process for ErythroMer's final and most stable form.

Design, Synthesis and Physico-Chemical Characterization of EM Presenting With 'bait' Functionalities.

Figure 4A:
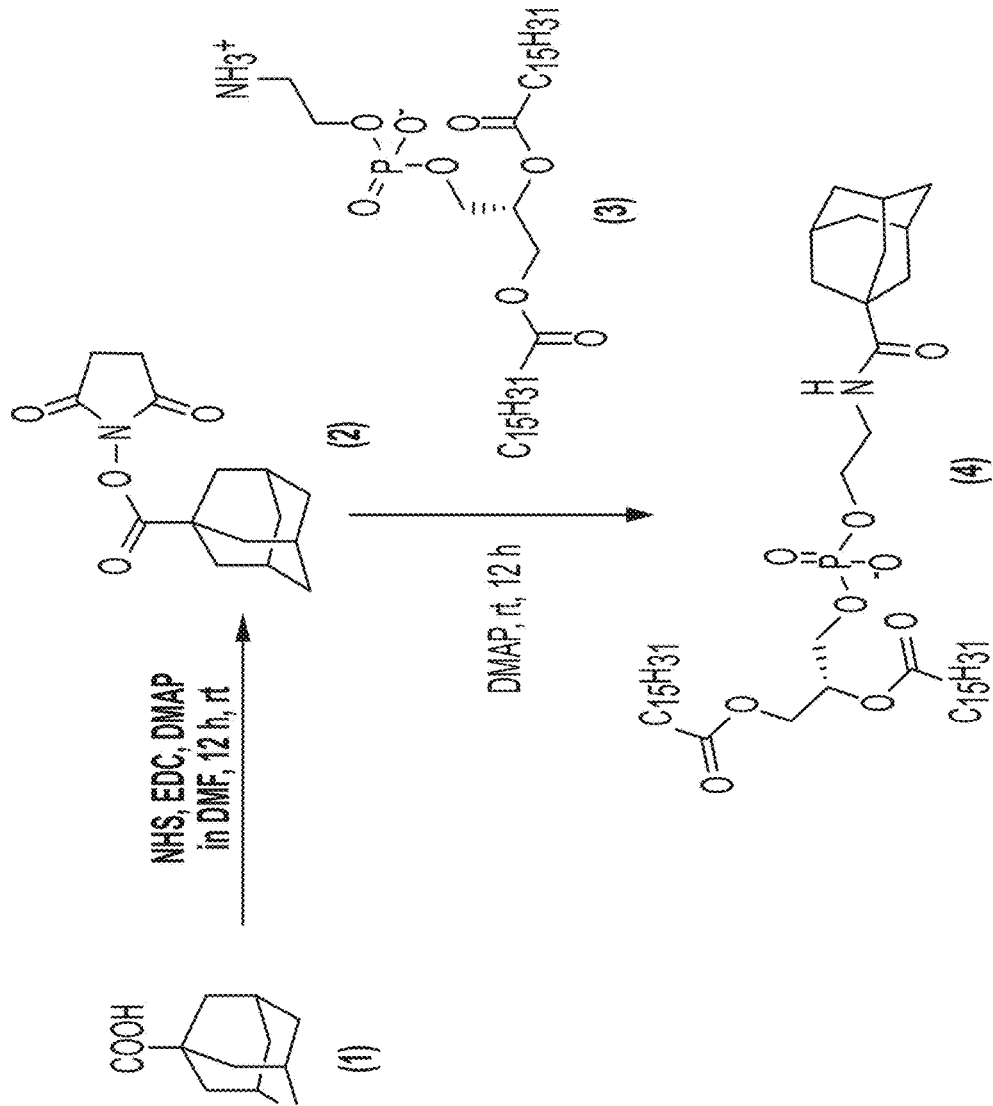
FIG. 4A shows a scheme for synthesis of 'bait' component adamantane functionalized DPPE (ADM-DPPE)

Example 1. Design and synthesis of 'bait' tagged EM. EM tagged with ADM is prepared and the small molecules and the nanoparticles are physico-chemically characterized for supramolecular host-guest chemistry with β-CD containing resins. Amino (-NH2) groups 1,2-dipalmitoyl-sn-glycero-3-phosphoethanolamine (DPPE) are functionalized with ADM tags using 1-adamantane-carboxylic acid N-hydroxysuccinimide ester (ADM-NHS). (FIG. 4A) This compound, ADM-DPPE, is characterized analytically for their purity and introduced in the nano-assembly of EM at a varied molar ratio. The optimum concentration of ADM-DPPE tag on EM particles is then determined based on two parameters: (i) highest binding capability and (ii) optimum Hb encapsulation efficiency. Accordingly, the formulations having different ADM-tag ratios is first interacted with a fixed concentration of β-CD and the binding capabilities of the tagged EM particles are calculated from the respective isothermal calorimetry curves. The particle having the highest binding efficiency is chosen and the concentration of ADM-tag is used as the optimal one. Secondly, this optimized EM particle is then loaded with hemoglobin and the encapsulation efficiency is calculated.

Example 2. Physico-chemical characterization. We evaluate hydrodynamic particle size, polydispersity, and electrophoretic potential, TEM, AFM, and stability. To determine the long-term storage stability of EM-1003-bait, a 12-month study is performed at −20° C., 5° C., 25° C., and under the accelerated condition of 40° C. (lyophilized EM is spread on a glass dish to have a thin homogeneous layer). Thermal (dry heat) accelerated stress stability analysis is performed up to 12 months at 40° C., 50° C., and 60° C. and for one month at 80° C. EM is also subjected to thermal stress at 25° C. and 40° C. under acidic (0.1 M HCl: pH 1; 0.01 M HCl: pH 2; HCl: pH 4.5) and alkaline (0.1 M NaOH: pH 13; 0.01 M NaOH: pH 12) conditions up to 7 days. The pH of all the solutions is measured using a pH meter at RT. The particle size and colloidal stability over different time intervals are measured using the Nanosizer ZS and ZetaView.

Development and Characterization of a 'capture' Resin and Demonstration of Separation Capability.

Figure 4B:
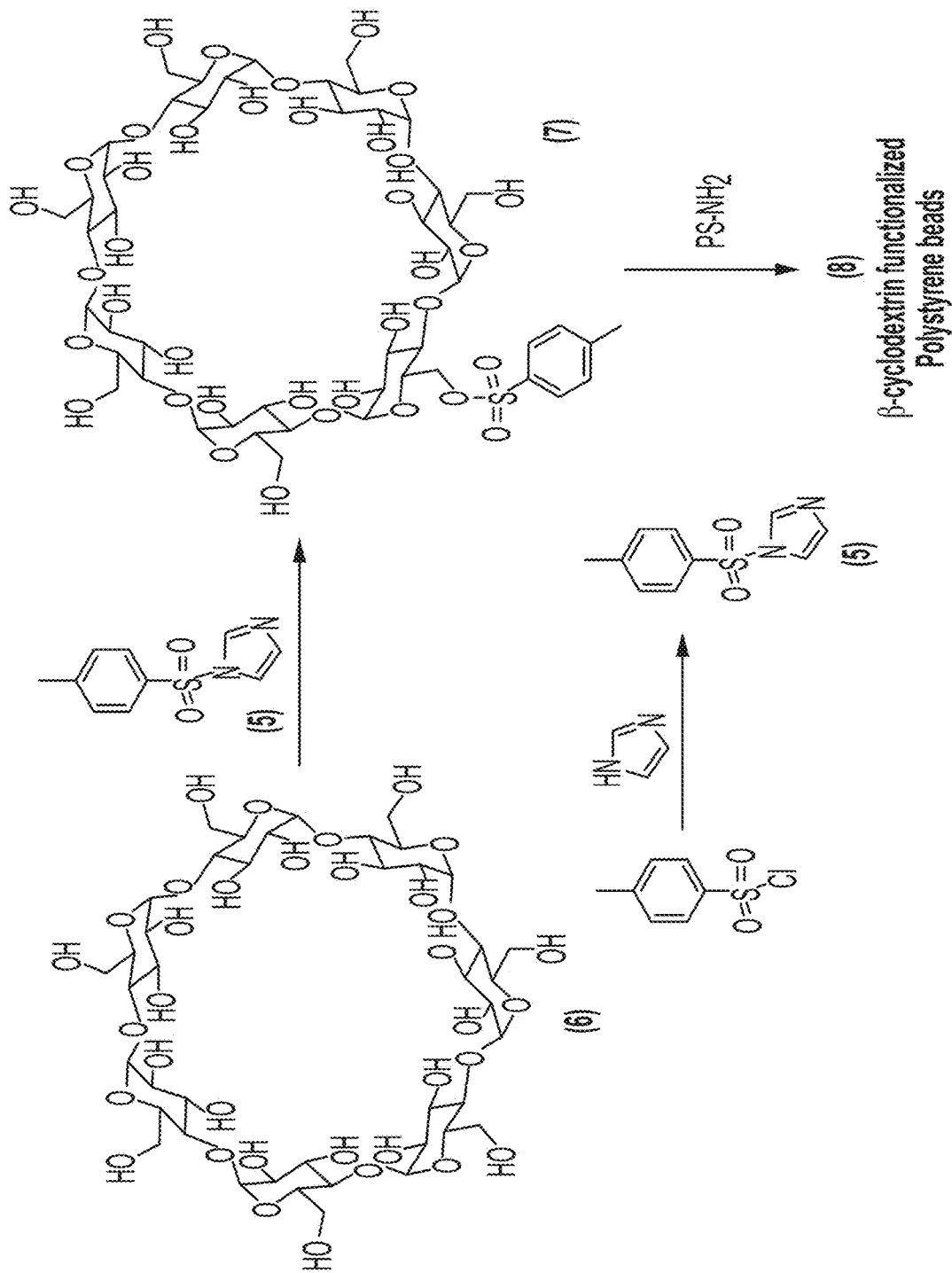
FIG. 4B shows a scheme for synthesis of capture agent β-cyclodextrin functionalized PS beads (CD-PS).
Figure 5:
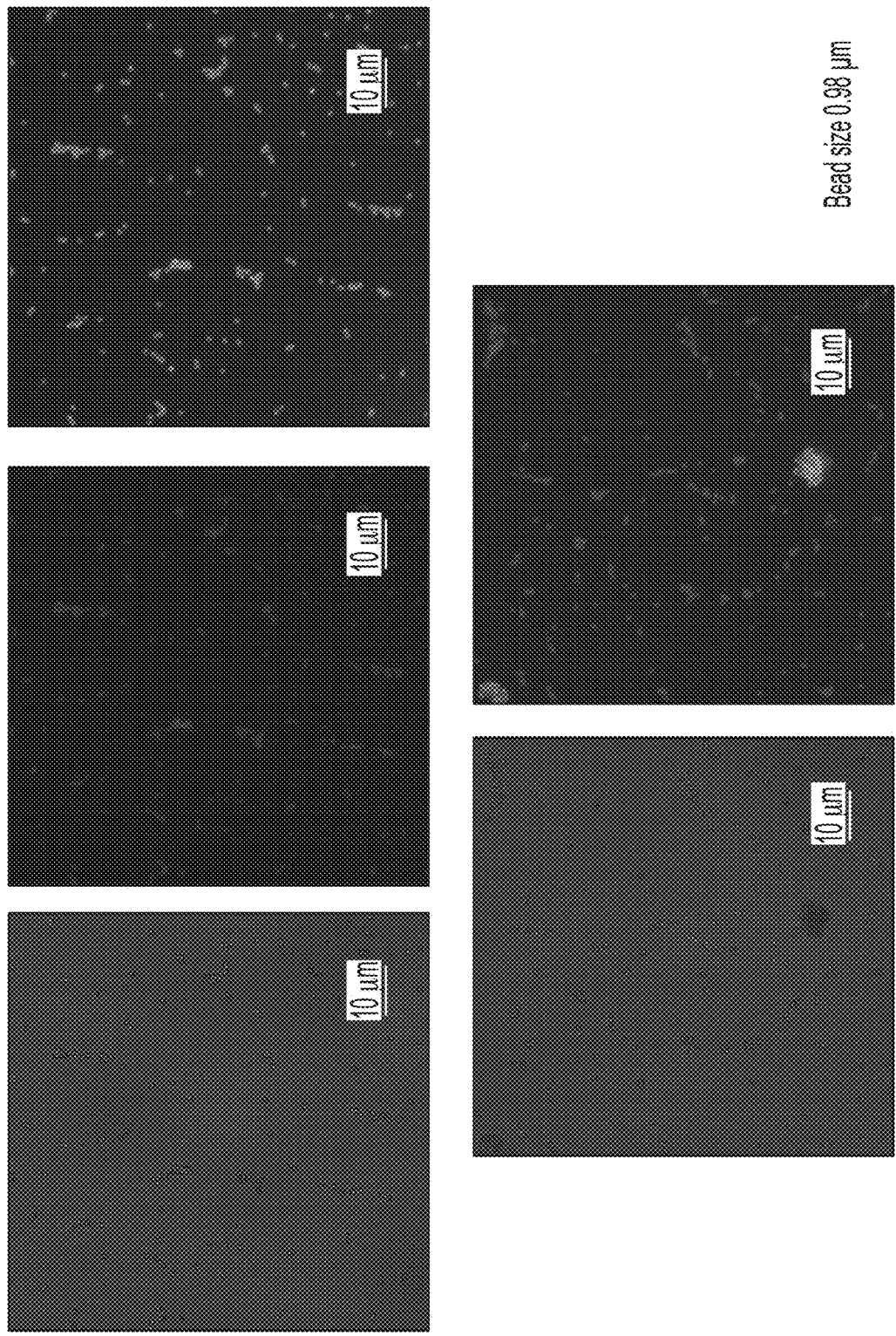
FIG. 5 shows confirmation of β-DC functionalization on PS beads (incubated with pyrene; bead size 0.98 nm).
Figure 6B:
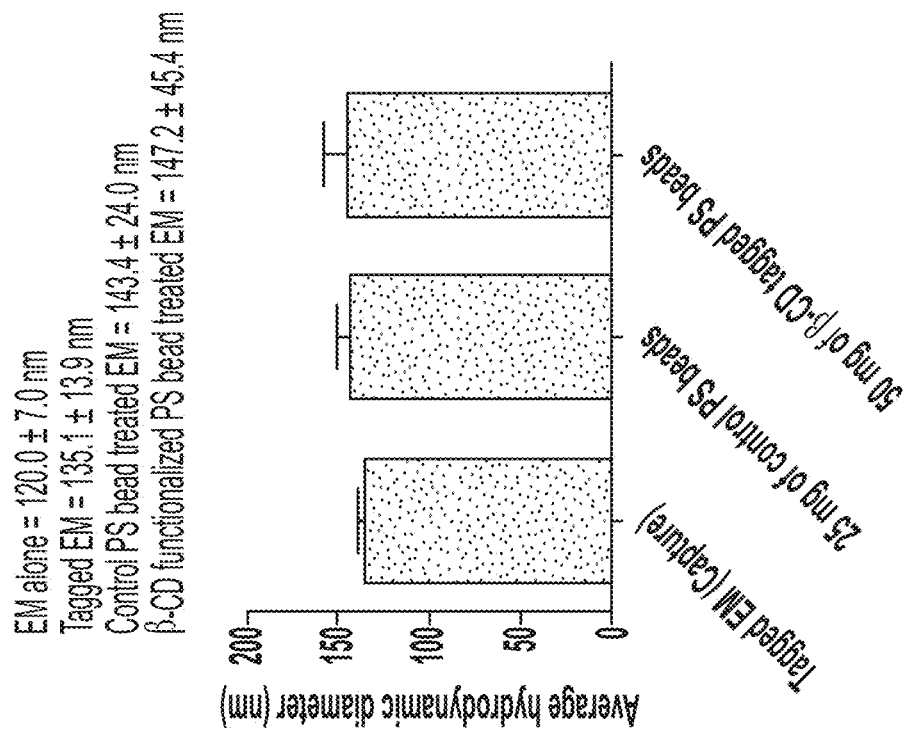
FIG. 6B shows confirmation of EM capture by diameter after capture using nanoparticle tracking analysis (ZetaView).
Figure 6A:
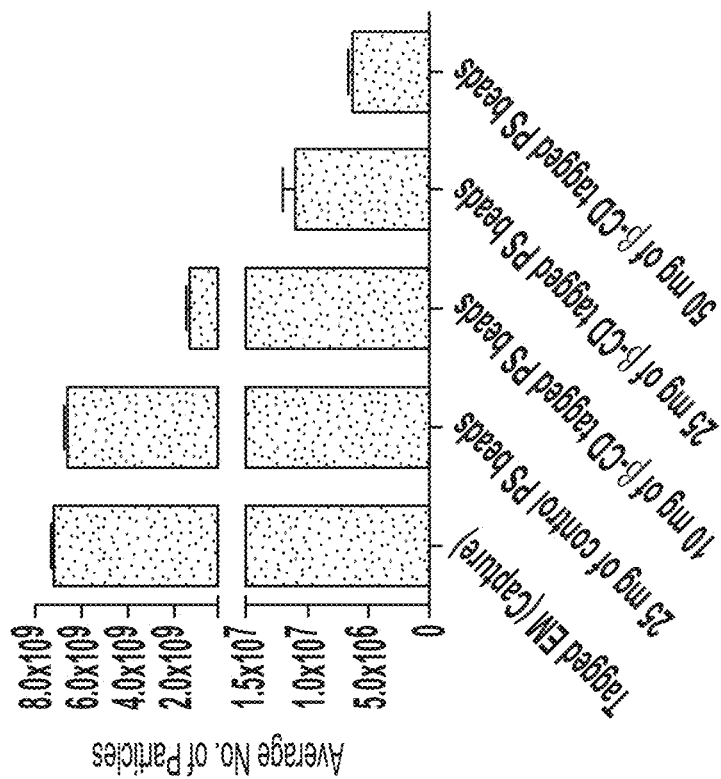
FIG. 6A shows confirmation of EM capture by particle count using nanoparticle tracking analysis (ZetaView).
Figure 7:
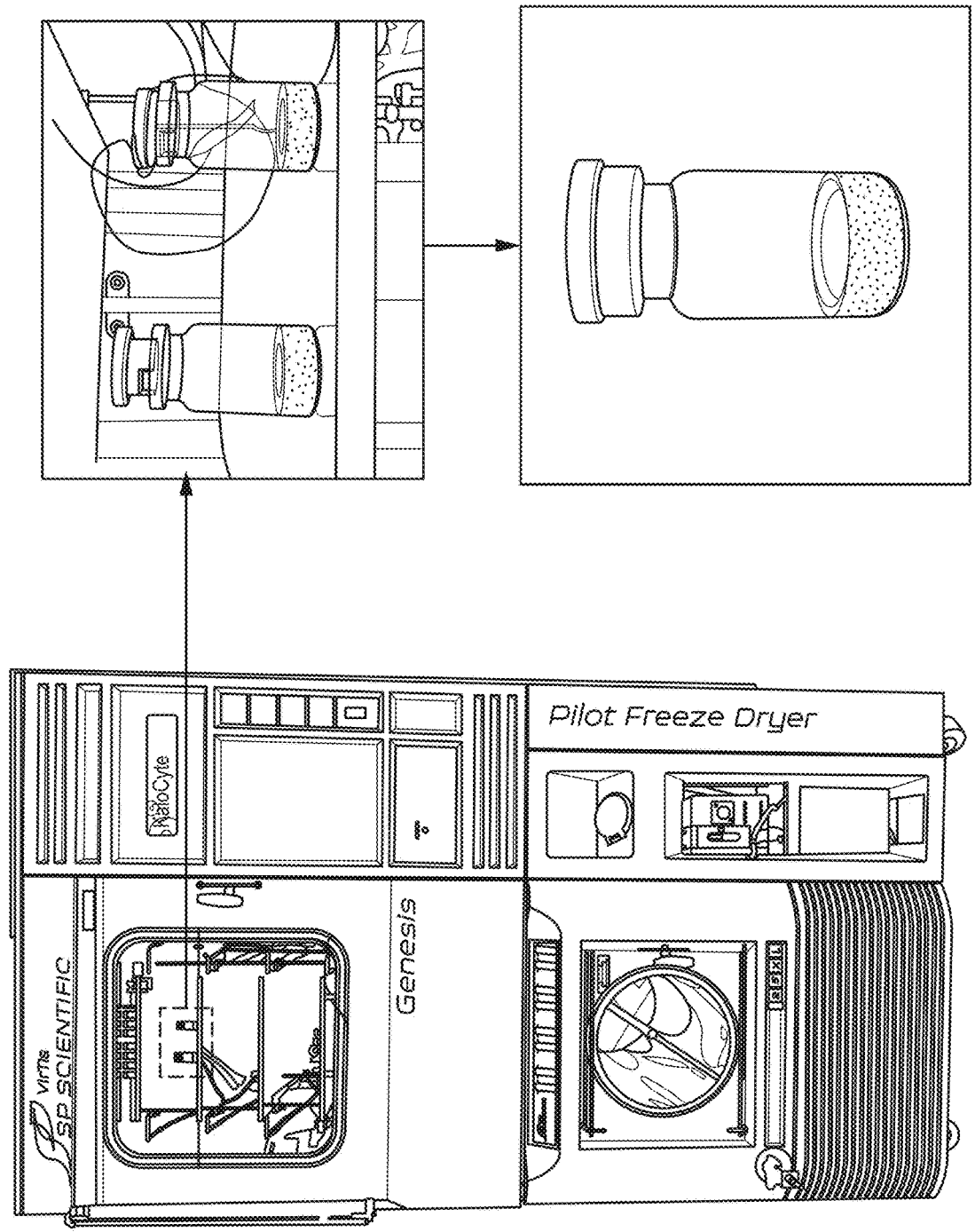
FIG. 7 is a representation of lyophilization and final lyophilized AM-tagged EM product according to an embodiment of the invention.

Example 3. Preparation and characterization of the capture resin: β-Cyclodextrin is often used as the host carrier in a host-guest supramolecular assembly because of its water solubility, low cytotoxicity and superior biocompatibility. In this context, we prefer the ADM/β-CD host—guest pair as a well-established supramolecular system. Mono-6-O-(p-toluenesulfonyl)-β-cyclodextrin is synthesized from 1-(p-Toluenesulfonyl) imidazole and β-cyclodextrin. This compound is then used for the functionalization of amino polystyrene (NH2-PS) beads to produce β-cyclodextrinylated PS (CD-PS) beads under mild alkaline condition. (FIG. 4B) To confirm the successful functionalization of the PS beads with β-cyclodextrin, the CD-PS beads are mixed with a ethanolic solution of pyrene, centrifuged at 10000 rcf for 2 mins, washed with ethanol twice to remove any free pyrene and then imaged under a fluorescence microscope to visualize the fluorescence of the functionalized beads. The successfully functionalized PS beads show high green emission, while the unfunctionalized beads do not demonstrate any background fluorescence. (FIG. 5) This confirms the successful preparation of the capture resin, ready to be tested with the ADM-DPPE tagged EM particles.

Example 4. Demonstration of EM capture from a mixture of EM and blood: To demonstrate EM capture mediated by the CD-PS beads, the optimized ADM-tagged EM particles with fluorescent NBD-PE doping is prepared. In a similar manner, CD-PS beads are treated with these fluorescently tagged EM particles, suspended in buffer, centrifuged, washed and imaged under fluorescent microscope. After successfully validating the capture of EM particles by CD-PS beads, the ADM-tagged EM particles are loaded with hemoglobin. The Hb loaded ADM-tagged EM particles are then suspended with blood and the capture of EM particles is monitored from the whole blood specimens.

Example 5. Demonstration and optimization of the EM surface: The % functionalization of β-CD to the PS beads is calculated from pH titration. The change in neutralization pH is compared between the unfunctionalized amino PS beads and CD-PS beads and the % functionalization of β-CD per gm of PS beads is calculated. The ratio of β-CD per gm of PS beads is then varied by controlling the concentration of mono-6-O-(p-toluenesulfonyl)-β-cyclodextrin reacted with amino PS beads. The optimum concentration of β-CD is then selected based on their maximum efficiency of EM removal from the whole blood specimen.

Example 6. Preliminary biocompatibility studies. Preliminary complement activation analysis and blood smear preparation studies is conducted. The CH50 enzyme immunoassay (EIA) (Sigma) is used to evaluate the magnitude of complement activation as a result of the addition of EM-1003-Bait to human serum. The kit is used according to the manufacturer's protocol. A blood smear preparation is performed to observe morphological changes in lymphocytes and blood clumping using clinical microscopy technique (conventional light microscopy) under high power field. Particular attention is paid to observe significant clumping or morphological changes in blood cells treated with EM-1003 and EM-1003-Bait (blood: NP=9:1)

Anticipated Results and Risk Factors. EM particle with ADM functional groups on the surface is synthesized. Mono-6-O-(p-toluenesulfonyl)-β-cyclodextrin is synthesized from 1-(p-Toluenesulfonyl) imidazole and β-CD and used for the functionalization of amino polystyrene (NH2-PS) beads to produce CD-PS beads. This invention validates the capture of EM particles by CD-PS beads with and without the encapsulation of Hb. The Hb loaded Ad-tagged EM particles are suspended with blood and the capture of EM particles is monitored. Further CBC and metabolic panel analyses are conducted to confirm the successful disappearance of EM interference. The supramolecular approach of the invention brings several advantages, e.g. (i) facile formation of the inclusion complex under ambient condition makes the pilot-scale study feasible without introducing any special genetic or biochemical techniques; (ii) the relatively small ADM-tag is expected to have little to none effect on the EM structures and functions and (iii) the optimal ratio of β-CD functionalization on PS beads introduces insignificant changes to the pore size of the column beads and hence safely clear the blood stream.

From our preliminary capture studies, EM was found to be successfully captured by the capture resin. (FIG. 6) It was observed that average number of EM particles decreased only when treated with β-CD tagged capture resin. Increased concentration of CD-PS decreased EM particles significantly (FIG. 6A). Further it has been observed that the average hydrodynamic diameter of the EM particles increased after successful capture mediated by the β-CD tagged resin (FIG. 6B). If EM stability becomes an issue, the 'bait' functional groups may be optimized to reach the maximum stability.

The adamantane-tagged EM is lyophilized for packaging, transport and/or storage. The lyophilized adamantane-baited EM is a powder comprising EM amphiphilic precursor, cholesterol and PEG-PE hemoglobin and allosteric effector, the adamantane tag, and optionally also including cryoprotectants. Reconstitution at the original EM production concentration (or concentrated) is achieved with PBS/water by simple mixing and gentle vortexing/agitation.

It is noted that the bait and capture methods and compositions described herein may be used to remove any type of biosynthetic nanoparticle from any bodily fluid or constituent part thereof While several embodiments and methodologies of the present disclosure have been described and shown in the drawings, it is not intended that the present disclosure be limited thereto, as it is intended that the present disclosure be as broad in scope as the art will allow and that the specification be read likewise. Therefore, the above description should not be construed as limiting, but merely as exemplifications of particular embodiments and methodologies. Those skilled in the art will envision other modifications within the scope of the claims appended hereto.

The invention claimed is:

1. A method for removing a nano-particle from a bodily fluid comprising: complexing an adamantane compound to a nano-particle, administering to a subject the nano-particle complexed to said adamantane compound, and subsequently contacting the bodily fluid with mono-6-O-(p-toluenesulfonyl)-β-cyclodextrin functionalized polystyrene beads, to remove said nano-particle complexed to said adamantane compound from said bodily fluid, wherein the adamantane compound has the formula:

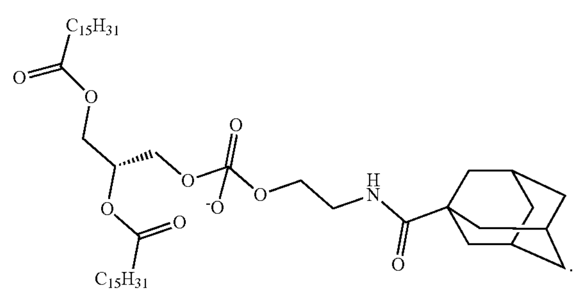

2. A method according to claim 1 wherein the nano-particle is a synthetic oxygen-carrier substitute and the bodily fluid is whole blood.

3. The method according to claim 1, further comprising lyophilizing a result of said complexing step for packaging and transport, and reconstituting a result of said lyophilizing step prior to said administering step.

4. The method of claim 1, wherein adamantane functional groups of said adamantane compound are located on a surface of the nano-particle.

5. The method of claim 1, wherein the nano-particle is a synthetic oxygen carrier substitute.

6. The method of claim 1, wherein functional groups of said adamantane compound are located on a surface of the nano-particle.

* * * * *